(12) United States Patent
Hijlkema

(10) Patent No.: US 6,962,604 B2
(45) Date of Patent: Nov. 8, 2005

(54) FLEXIBLE ENDOLUMINAL STENT AND PROCESS OF REPAIRING A BODY LUMEN

(75) Inventor: Lukas J. Hijlkema, Co. Galway (IE)

(73) Assignee: SciMed Life Systems, Inc., Maple Grove, MN (US)

(*) Notice: Subject to any disclaimer, the term of this patent is extended or adjusted under 35 U.S.C. 154(b) by 453 days.

(21) Appl. No.: 09/777,387

(22) Filed: Feb. 6, 2001

(65) Prior Publication Data
US 2001/0010015 A1 Jul. 26, 2001

Related U.S. Application Data

(63) Continuation of application No. 09/412,817, filed on Oct. 5, 1999, now Pat. No. 6,302,907.

(51) Int. Cl.⁷ .................................. A61F 2/00
(52) U.S. Cl. ............... 623/1.15; 606/194; 606/192; 606/195; 606/198; 623/1.22
(58) Field of Search ............... 623/1.15–1.22; 606/192–194, 195–198, 108, 191

(56) References Cited

U.S. PATENT DOCUMENTS

| | | | |
|---|---|---|---|
| 5,135,536 A | * | 8/1992 | Hillstead .................. 606/195 |
| 5,549,662 A | * | 8/1996 | Fordenbacher ............. 623/1.17 |
| 5,613,981 A | | 3/1997 | Boyle et al. |
| 5,643,339 A | | 7/1997 | Kavteladze et al. |
| 5,746,766 A | | 5/1998 | Edoga |
| 5,766,237 A | * | 6/1998 | Cragg ..................... 606/194 |
| 5,800,515 A | | 9/1998 | Nadal et al. |
| 5,843,158 A | | 12/1998 | Lenker et al. |
| 5,855,596 A | | 1/1999 | Acciai et al. |
| 6,015,432 A | | 1/2000 | Rakos et al. |
| 6,033,436 A | * | 3/2000 | Steinke et al. ............ 623/1.15 |
| 6,090,127 A | | 7/2000 | Globerman |
| 6,117,165 A | | 9/2000 | Becker |
| 6,224,626 B1 | * | 5/2001 | Steinke ................... 623/1.16 |

FOREIGN PATENT DOCUMENTS

FR  2 765 097   12/1998
WO  WO 99/44535   9/1999

OTHER PUBLICATIONS

International Search Report in corresponding International Application PCT/US00/27075, mail date: Jan. 24, 2001.

* cited by examiner

Primary Examiner—Vy Bui
(74) Attorney, Agent, or Firm—RatnerPrestia

(57) ABSTRACT

A generally tubular intraluminal compound stent comprising a plurality of component stents, each component stent having a length and a plurality of individual hoops axially disposed along the length and connected by a connecting spine, the component stents meshed with one another such that at least one hoop of one component stent is positioned between axially adjacent hoops of another component stent. The connecting spines may be helical, with at least one component stent spine oriented in a different helical direction than the spine of another component stent. Each hoop may further have a periphery comprising a pattern of zigzags having apices, wherein adjacent hoops of the meshed component stents are aligned such that the apices of adjoining hoops abut or are interdigitated with one another. The compound stent may further comprise connectors, such as sutures, connecting at least some of the abutting or interdigitated apices. A process for manufacture of a flexible endoluminal compound stent is also disclosed.

27 Claims, 3 Drawing Sheets

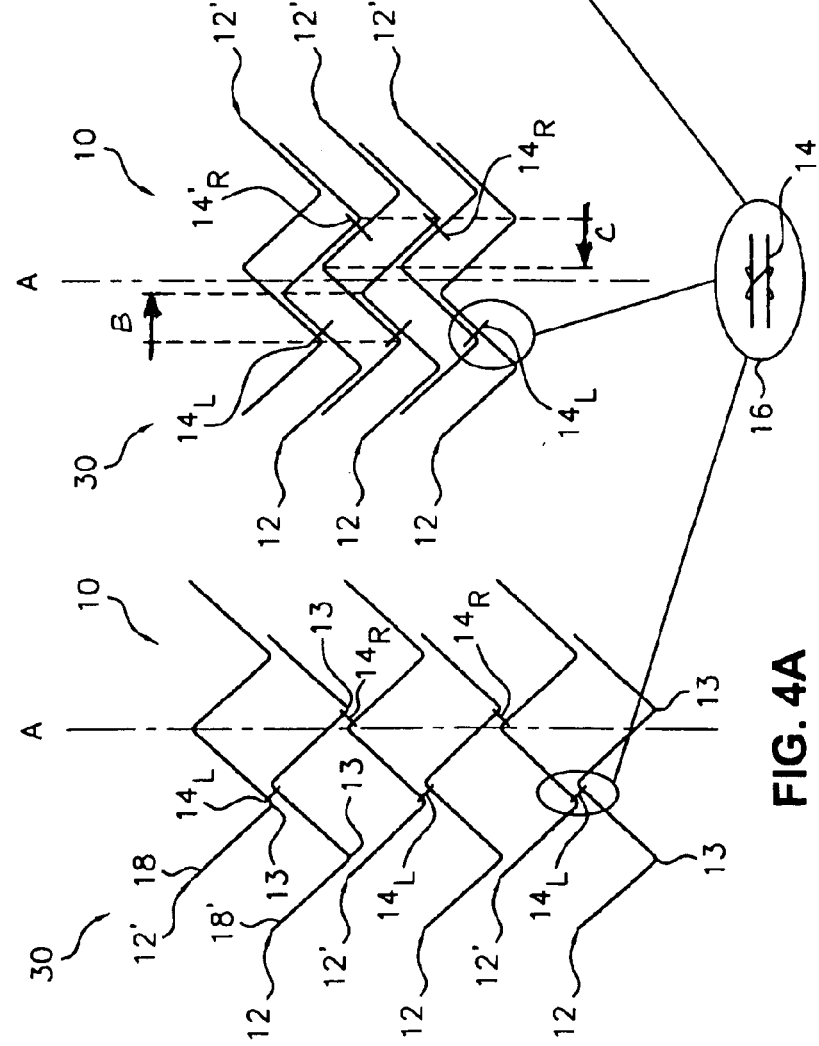

FLEXIBLE ENDOLUMINAL STENT AND PROCESS OF REPAIRING A BODY LUMEN

RELATED APPLICATION INFORMATION

This application is a continuation of application Ser. No. 09/412,817, filed Oct. 5, 1999 now U.S. Pat. No. 6,302,907.

TECHNICAL FIELD

The present invention relates generally to endoluminal grafts or "stents" and, more specifically, to a flexible stent advantageous for use in a curved or tortuous lumen.

BACKGROUND OF THE INVENTION

A stent is an elongated device used to support an intraluminal wall. In the case of a stenosis, a stent provides an unobstructed conduit for blood in the area of the stenosis. An intraluminal prosthesis may comprise a stent that carries a prosthetic graft layer of fabric. Such a prosthesis may be used, for example, to treat a vascular aneurysm by removing the pressure on a weakened part of an artery so as to reduce the risk of rupture. Typically, an intraluminal stent or prosthesis is implanted in a blood vessel at the site of a stenosis or aneurysm endoluminally, i.e. by so-called "minimally invasive techniques" in which the stent, restrained in a radially compressed configuration by a sheath or catheter, is delivered by a stent deployment system or "introducer" to the site where it is required. The introducer may enter the body through the patient's skin, or by a "cut down" technique in which the entry blood vessel is exposed by minor surgical means. When the introducer has been threaded into the body lumen to the stent deployment location, the introducer is manipulated to cause the stent to be ejected from the surrounding sheath or catheter in which it is restrained (or alternatively the surrounding sheath or catheter is retracted from the stent), whereupon the stent expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Some locations in which stents may be implanted are tortuous in nature, such as the aortic arch for thoracic aneurysm treatment. Additionally, the aneurysm may gradually change in volume after implantation of the stent (known in the art as D3 and H3 shrinkage). Known stents may not be flexible enough to adjust to the tortuosity of the lumen along its length or to changes in the aneurysm after implantation. Thus, it would be useful to have a more flexible stent to accommodate such situations.

SUMMARY OF THE INVENTION

The present invention comprises a generally tubular intraluminal compound stent comprising a plurality of component stents, each component stent having a length and a plurality of individual hoops axially disposed along the length and connected by a connecting spine. The component stents are meshed with one another such that at least one hoop of one component stent is positioned between axially adjacent hoops of another component stent. Each component stent may comprise a single wire, each hoop comprising a circumferential winding of the wire, and the connecting spine comprising at least one connecting spine member comprising an extension of the wire between adjacent hoops. Each connecting spine may traverse each component stent circumferentially in a helical pattern, wherein the spine of at least one component stent is oriented in a different helical direction than the helical direction of the spine of another component stent in the compound stent. The compound stent may consist essentially of a first component stent having a first connecting spine and a second component stent having a second connecting spine. The hoops of the first component stent may be axially interspersed with the hoops of the second component stent in an alternating pattern, such as a single hoop alternating pattern. The first connecting spine may be helically oriented in a clockwise direction and the second connecting spine oriented in a counter-clockwise direction.

Each hoop may further have a periphery comprising a pattern of zig-zags having apices, wherein adjacent hoops of the meshed stents are aligned such that the apices of adjoining hoops abut or are interdigitated with one another. The compound stent may further comprise connectors, such as sutures, connecting at least some of the abutting or interdigitated apices.

The invention also comprises a process for manufacture of a compound stent having a length, the method comprising creating a plurality of component stents, each component stent having a length and a plurality of hoops axially disposed along the length and connected by a connecting spine. The process comprises meshing the plurality of component stents together such that at least one hoop of one component stent is positioned between axially adjacent hoops of another component stent. Each hoop of each stent may further comprise a pattern of zig-zags having apices in which case the method further comprises meshing the component stents so that the apices of adjacent hoops of the meshed component stents abut or are interdigitated with one another. The process may further comprise connecting at least some of the abutting or interdigitated apices with one another. Creating each component stent may comprise creating each component stent by winding a single wire circumferentially to form each hoop and extending connecting spine members between adjacent hoops, aligning the connecting spine members such that the connecting spine members collectively form a connecting spine oriented in a helical pattern. In such case, the process further comprises creating at least one of the component stents with a connecting spine that traverses the component stent in a helical orientation opposite the helical orientation of the connecting spines of the other component stents, so that meshing the component stents together comprises crossing the oppositely-oriented helical spines in at least one location along the compound stent.

It is to be understood that both the foregoing general description and the following detailed description are exemplary, but are not restrictive, of the invention.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIGS. 4A–4C are schematic side view illustrations of the exemplary compound stent of FIG. 3 in a flexed configuration viewed along an inner radius of curvature, showing differing amounts of overlap between successive hoops at varying radii of curvature.

DETAILED DESCRIPTION OF INVENTION

Figure 3:
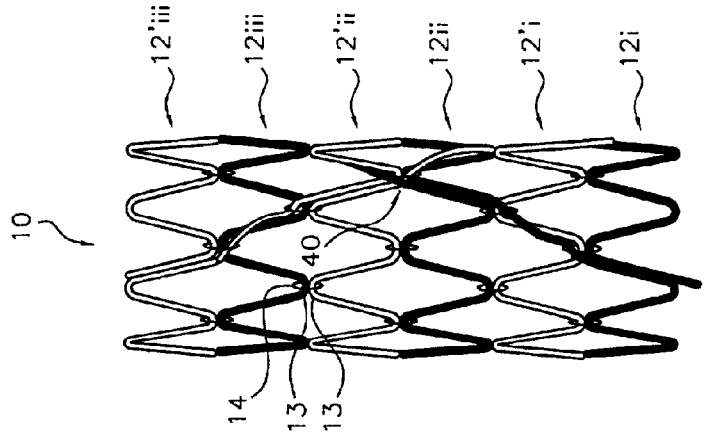
FIG. 3 is a side view illustration of an exemplary compound stent of the present invention comprising the component stents of FIG. 1B and FIG. 2B meshed together.

Referring now to the drawing, FIGS. 1A–4 illustrate various aspects of an intraluminal compound stent according to the present invention. Generally, compound stent 10 is a tubular stent comprising a plurality of hoops 12$i$–$iii$ and 12'$i$–$iii$ disposed axially along the length of the stent. Compound stent 10 comprises two component stents 20 and 20' joined together: a first component stent 20 having a plurality of axially-disposed individual hoops 12$i$–$iii$ and a connecting spine 22, and a second component stent 20' having a plurality of axially-disposed individual hoops 12'$i$–$iii$ and a connecting spine 22'. The hoops of the first and second component stents are meshed together so that at least one hoop of one component stent is positioned between axially adjacent hoops of the other component stent, as shown in FIG. 3. For example, hoop 12'$i$ is positioned between hoops 12$i$ and 12$ii$, hoop 12$ii$ is positioned between hoops 12'$i$ and 12'$ii$, and so on.

As shown in FIG. 3, hoops 12$i$–$iii$ and 12'$i$–$iii$ of stents 20 and 20', respectively, are meshed with one another in a single hoop alternating pattern. "Single hoop alternating pattern" as used herein means that the hoops alternate one hoop from stent 20, one hoop from stent 20', and so on, traversing compound stent 10 in an axial direction. The alternating pattern of stent 10 may be represented by a shorthand such as 1:1:1:1:1:1, indicating that there are 6 hoops overall, alternating one at a time. Other stents may be constructed in a two or other multiple-hoop alternating pattern (2:2:2:2) or in a non-homogeneous alternating pattern (3:2:2:3, 1:2:1, etc.). Compound stents comprising more than two component stents may also be constructed.

Figure 1A:
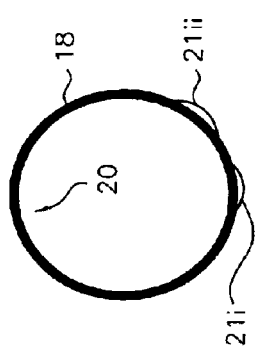
FIGS. 1A and 1B are end and side views, respectively, of an exemplary first component stent of the present invention in isolation.
Figure 1B:
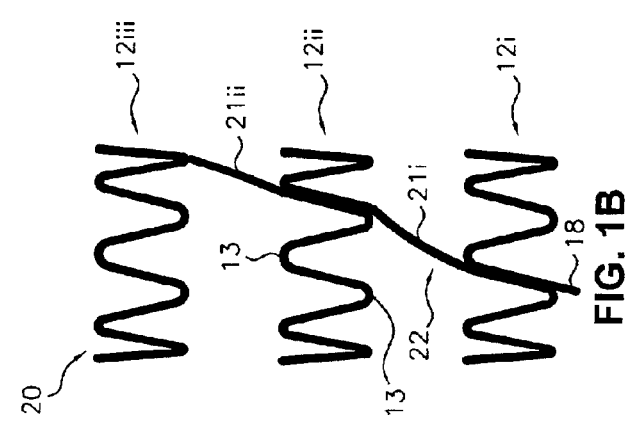

Each hoop 12 and 12' of stents 20 and 20' comprises a pattern of zig-zags between apices 13, as shown in FIGS. 1A–3. As shown in FIG. 3, abutting apices 13 of hoops 20 and 20' may be connected together by sutures 14, as is well known in the art. As shown in FIGS. 1A and 1B, hoops 12 of stent 20 may be formed of a continuous wire 18 that winds circumferentially in a zig-zag pattern to make a first hoop 12$i$, then forms a spine member 21$i$, then hoop 12$ii$, and so on. The combination of spine members 21$n$ between hoops 12$n$ and 12$n$+1 collectively form spine 22, which wraps around the circumference of the stent in a helical pattern. As shown in FIGS. 1A and 1B, spine 22 wraps about stent 20 in a helical counter-clockwise fashion, as viewed from hoop 12$iii$ looking in the direction of hoop 12$i$.

Figure 2A:
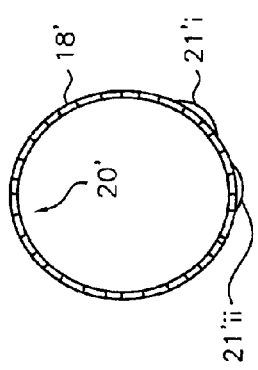
FIGS. 2A–2B are end and side views, respectively, of an exemplary second component stent of the present invention in isolation.
Figure 2B:
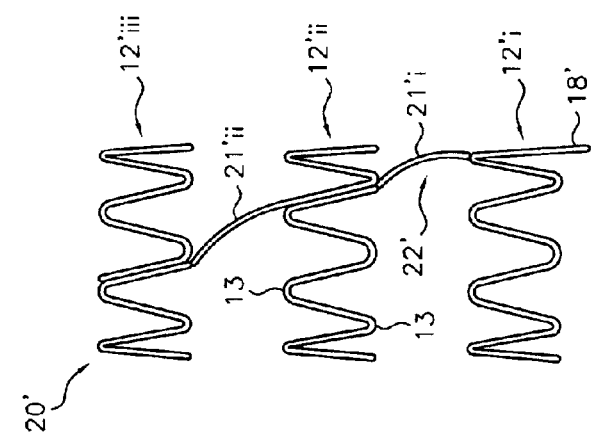

Similarly, stent 20', as shown in FIGS. 2A and 2B, comprises wire 18' wound into corresponding hoops 12'$i$–$iii$ and connecting segments 21'–$ii$ of spine 22' in what is essentially a mirror image of stent 20. As shown in FIGS. 2A and 2B, spine 22' wraps about stent 20' in a helical clockwise fashion, as viewed from hoop 12'$iii$ looking in the direction of hoop 12'$i$. As shown in FIG. 3, the two stents 20 (dark wires 18) and 20' (light wires 18') come together to form compound stent 10. Although only three hoops 12 or 12' are shown on each stent 20 and 20' to conserve space in FIGS. 1A–3, compound stent 10 may comprise as many hoops as necessary to reach the desired length.

Wires 18 and 18' may comprise a shape-memory material, such as nitinol. Although shown as single-wire, helical-spine stents in FIGS. 1A–3, component stents may be formed of compound stents having multiple wires, having non-helical spines or spines where the helical or other pattern is broken into discrete sections between adjacent hoops rather than aligned in a continuous spine, or having a spine that comprises a separate wire from the wire comprising the hoops.

FIGS. 4A–4C are side views of a curved portion of compound stent 10 at the inner radius of that curvature, showing how the apices 13 of adjacent pairs of hoops 12 and 12' may slip relative to one another and become interdigitated when compound stent 10 is flexed. As used herein, the term "interdigited" means that a portion of one hoop extends axially into the axial length defined by an adjacent hoop. Thus, FIG. 4A shows a curved portion having a radius of curvature "R" that is greater than the radius of curvature for FIGS. 4B and 4C, with FIG. 4C illustrating the smallest radius of curvature, or the most flexed state, of the three related figures.

The slippage direction of apices 13 of adjacent hoops 12 and 12' relative to one another may prevent torsional forces from developing in compound stent 10. The helical orientation of spines 22 and 22' in opposite directions from one another may facilitate and direct such slippage. The apices of hoops 12 tend to slip in the direction of arrow "B" and the apices of hoops 12' tend to slip in the direction of arrow "C", producing substantially a net zero torsional resultant force on compound stent 10. Even if one or more hoops slip in the opposite direction than expected, other hoops may compensate for such misdirection, making the overall resultant still substantially zero. Providing a substantially zero resultant force is desirable so that stent 10 may be flexed either at or after deployment to meet the tortuous curvature of the lumen in which it is implanted without torsional resistance forces potentially affecting the integrity of any seal between the stent and the lumen. To achieve such a substantially zero resultant, each component stent having opposite helical spines preferably has the same number of hoops.

Because spines 22 and 22' circumscribe component stents 20 and 20', respectively, in opposite rotational directions, the spines have overlapping sections 40 at regular intervals, as shown in FIG. 3. Overlapping section 40 may be a less flexible section than the remainder of the compound stent 10, and such overlaps may be integrated into the overall stent design to provide flexibility and rigidity where desired. Where more than two component stents are meshed together to form a compound stent, overlapping sections may be distributed in a particular pattern to provide stiffness where desired. In particular, it may be desirable to distribute overlapping sections so that each is spaced circumferentially 180° from another. The more component stents meshed together, the more such overlapping sections created and the stiffer the resulting compound stent.

Abutting apices 13 of adjacent hoops 12 and 12' are connected to one another with connectors 14, which may be sutures as shown in detail oval 16 of FIG. 4B. During flexion of compound stent 10, sutures or other connectors 14 connecting interdigitated apices 13 may tend to develop an angular orientation with respect to longitudinal axis A of the compound stent as shown in FIGS. 4A–4C. As shown, the angular orientation of successive connectors 14L and 14R along the length of compound stent 10 may even alternate in opposing directions with respect to longitudinal axis A.

Thus, connectors 14L may become oriented from axis A pointing to the left in the distal direction, whereas connectors 14R may become oriented from axis A pointing to the right in the distal direction. Slippage may still occur, however, without the sutures developing the particular angular orientation as illustrated by sutures 14L and 14R in FIGS. 4A–4C.

Although illustrated herein with respect to compound stents comprising only two stents having hoops meshed in an alternating fashion with one another, the invention may also comprise a stent having more than two such stents with hoops so meshed. Where more than two such stents are involved, at least one of the stents may have a helical spine that is oriented oppositely from the others. For example, a three-stent compound stent may comprise two clockwise spines and one counter-clockwise spine, or vice versa, whereas a four-stent compound stent may comprise two clockwise and two counter-clockwise or three in one direction and one in the opposite direction. The compound stent as disclosed herein may also comprise a liner of biocompatible graft material covering either the outside of the stent, the inside of the stent, or both.

Figure 5:
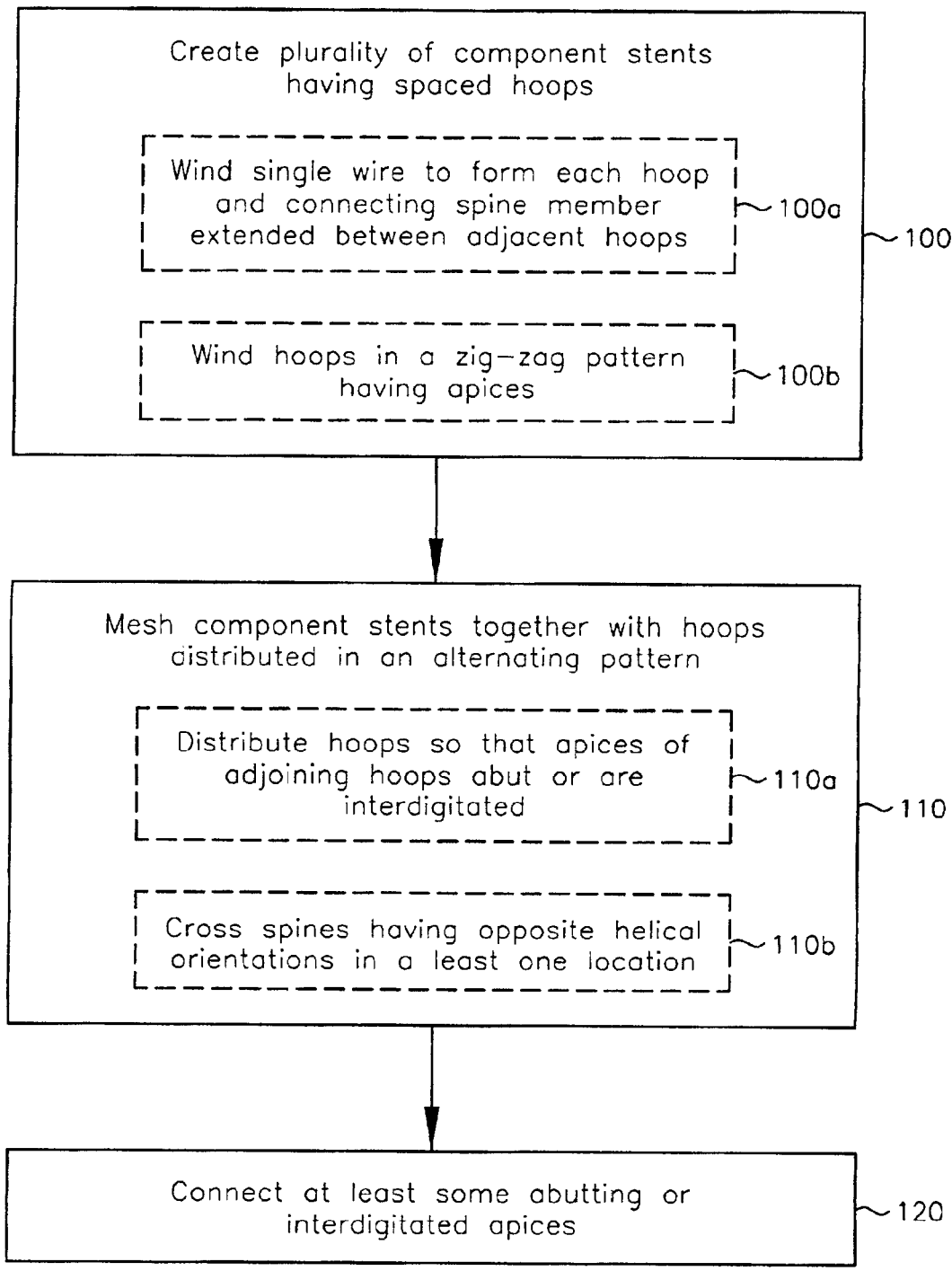
FIG. 5 is a flowchart depicting an exemplary process for manufacture of a stent of the present invention.

The present invention also comprises a process for manufacture of a compound stent as described and illustrated herein. Referring now to FIG. 5, there is shown a flowchart depicting an exemplary such process. The process comprises in step 100, creating a plurality of component stents such as stents 20 and 20' of FIGS. 1A–2B, each having a length and a plurality of individual hoops 12$i$–$iii$ and 12'$i$–$iii$ respectively, axially disposed along their length and each having a connecting spine 22 and 22', respectively. Forming each component stent in step 100 may further comprise step 100$a$ of winding a single wire, such as wires 18 and 18', on for example a mandrel, to form each hoop 12$i$–$iii$ and 12'$i$–$iii$ respective connecting spine members 21$i$–$ii$ and 21'$i$–$ii$ between adjacent hoops, each set of collective connecting spine members forming helically-oriented connecting spines 22 and 22'. Step 100$a$ may comprise creating at least one component stent having a connecting spine with a helical orientation opposite the helical orientation of a connecting spine in the another component stent, such as spine 22 that is helical counter-clockwise as compared to spine 22' that is helical clockwise. Forming each hoop in step 100$a$ may further comprise in step 100$b$, winding each hoop in a zig-zag pattern having apices 13.

Next, the process comprises in step 110, meshing the plurality of component stents together such that at least one hoop of one component stent is positioned between axially adjacent hoops of another component stent, such as hoop 12'$i$ of stent 20' meshed between hoops 12$i$ and 12$ii$ of stent 20 in compound stent 10 of FIG. 3. The meshing step 110 may further comprise step 110$a$ of distributing the hoops so that the apices of adjacent hoops of the meshed component stents abut or are interdigitated with one another, as is illustrated by abutting apices 13 in FIG. 3. Furthermore, the meshing step 110 may comprise in step 110$b$ meshing the plurality of component stents together such that the oppositely-orientated helical spines cross one another in at least one location along the compound stent, such as overlapping section 40 as shown in FIG. 3. Finally, in step 120, the process may further comprise connecting at least some of the abutting or interdigitated apices, such as sutures 14 and 14' shown connecting apices 13 in FIG. 5.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A generally tubular intraluminal compound stent having opposite ends and having a substantially zero resultant torsional force when deployed, the compound stent comprising a plurality of component stents, each component stent having a length and a plurality of individual hoops axially disposed along said length, a first connecting spine of a first component stent oriented in a first helical direction for connecting the individual hoops of the first component stent and a second connecting spine of a second component stent oriented in a second helical direction opposite the first helical direction for connecting the individual hoops of second component stent.

2. The compound stent of claim 1 wherein each said hoop of said first and second component stents further comprises a pattern of zig-zags having apices, the compound stent further comprising axially adjacent hoops of the meshed component stents aligned such that the apices of axially adjacent hoops abut or are interdigitated with one another and have connectors connecting at least some of said abutting or interdigitated apices.

3. The compound stent of claim 2 wherein the abutting or interdigitated apices are adapted to slip relative to one another.

4. The compound stent of claim 2 wherein the connectors are sutures.

5. The stent of claim 1 wherein the first spine crosses over the second spine in at least one location along the compound stent.

6. The stent of claim 5 wherein the first spine crosses over the second spine in a plurality of locations along the compound stent.

7. The stent of claim 6 wherein at least two locations where the first spine crosses the second spine are circumferentially spaced 180 degrees from one another.

8. A generally tubular intraluminal compound stent comprising a plurality of component stents, each component stent having a length and a plurality of individual hoops axially disposed along said length and connected by a connecting spine, at least a first connecting spine of a first component stent oriented in a first helical direction and a second connecting spine of a second component stent oriented in a second helical direction opposite the first helical direction, said component stents meshed with one another such that at least one hoop of one component stent is positioned between axially adjacent hoops of another component stent and the first spine crosses over the second spine in at least one location along the compound stent.

9. The stent of claim 7 wherein the first spine crosses over the second spine in a plurality of locations along the compound stent.

10. The stent of claim 9 wherein at least two locations where the first spine crosses the second spine are circumferentially spaced 180 degrees from one another.

11. The compound stent of claim 8 wherein each said hoop comprises a pattern of zig-zags having apices.

12. The stent of claim 8 wherein each hoop comprises a circumferential member.

13. A generally tubular intraluminal compound stent having opposite ends and adapted to exert when deployed a substantially zero resultant torsional force on a lumen, the compound stent comprising a plurality of discrete component stents, each component stent having a length and a plurality of individual hoops axially disposed along said length, wherein at least a first of said component stents comprises means for exerting a first torsional force in a first helical direction on the lumen when deployed and at least a second of said component stents comprises means for exerting a second torsional force in a second helical direction, opposite said first helical direction, on the lumen, wherein said second torsional force opposes said first torsional force to achieve said substantially zero resultant torsional force.

14. The stent of claim 13 wherein each component stent comprises a connecting spine for connecting the individual hoops of each component stent.

15. The stent of claim 13 comprising a first component stent and a second component stent wherein the first and second component stents are meshed with one another such that at least one hoop of the first component stent is positioned between axially adjacent hoops of the second component stent.

16. The compound stent of claim 15 wherein the stent consists of the first and second component stents.

17. The compound stent of claim 16 wherein the first component stent and the second component stent each have three hoops.

18. The compound stent of claim wherein 16 the hoops of said first component stent are axially interspersed with the hoops of said second component stent in an alternating pattern.

19. The compound stent of claim 18 wherein said alternating pattern of hoops comprises a single hoop alternating pattern.

20. The compound stent of claim 19 wherein the first component stent further comprises a first connecting spine and a first wire, each hoop of said first component stent comprising a circumferential winding of said first wire, said first connecting spine comprising at least one connecting spine member comprising an extension of said first wire between adjacent hoops of said first component stent, and wherein the second component stent further comprises a second connecting spine and a second wire, each hoop of said second component stent comprising a circumferential winding of said second wire, said second connecting spine comprising at least one connecting spine member comprising an extension of said second wire between adjacent hoops of said second component stent.

21. The compound stent of claim 20 wherein the first connecting spine is helically oriented in a clockwise direction and the second connecting spine is helically oriented in a counter-clockwise direction.

22. The compound stent of claim 13 wherein each said hoop comprises a pattern of zig-zags having apices.

23. The stent of claim 13 wherein each hoop comprises a circumferential member.

24. A generally tubular intraluminal compound stent comprising a plurality of discrete component stents, each component stent having a length and a plurality of individual hoops axially disposed along said length, said component stents meshed with one another such that at least one hoop of one component stent is positioned between axially adjacent hoops of another component stent, each of said hoops comprising a series of sinusoidal or zig-zag elements including apices alternatingly pointing in opposite directions along the axis of the stent, at least some of said apices of one hoop positioned relative to oppositely pointed apices of a facing adjacent hoop wherein said apices are adapted to slip axially and circumferentially relative to one another upon compression of said stent or a portion of said stent, and each hoop comprises a 360° circumference in which all apices pointing in a similar direction are substantially aligned on a single plane.

25. The stent of claim 24 wherein at least some of said facing, offset, oppositely pointing apices are connected to one another by separate connecting members.

26. The stent of claim 25 wherein said connecting members comprise sutures.

27. The stent of claim 24 wherein said stent comprises nitinol.

\* \* \* \* \*